(12) United States Patent
Tseng et al.

(10) Patent No.: US 9,820,846 B2
(45) Date of Patent: Nov. 21, 2017

(54) TUBULAR VASCULAR GRAFT AND THE PREPARATION THEREOF

(71) Applicant: National Tsing Hua University, Hsinchu (TW)

(72) Inventors: Fan-Gang Tseng, Hsinchu (TW); Shueh-Yao Chu, Hsinchu (TW); Chiao-Wen Chu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 170 days.

(21) Appl. No.: 14/686,262

(22) Filed: Apr. 14, 2015

(65) Prior Publication Data

US 2016/0166374 A1    Jun. 16, 2016

(30) Foreign Application Priority Data

Dec. 12, 2014 (TW) ............................. 103143461 A

(51) Int. Cl.
| | |
|---|---|
| *A01N 63/00* | (2006.01) |
| *A01N 65/00* | (2009.01) |
| *C12N 5/00* | (2006.01) |
| *A61F 2/06* | (2013.01) |
| *B05D 1/18* | (2006.01) |

(52) U.S. Cl.
CPC ............... *A61F 2/062* (2013.01); *B05D 1/18* (2013.01); *B05D 2254/02* (2013.01)

(58) Field of Classification Search
None
See application file for complete search history.

(56) References Cited

PUBLICATIONS

Merriam-Webster Online Dictonary, <http://www.merriam-webster.com/dictionary/reparation> (Accessed Nov. 29, 2016).*
Chen et al., Adv. Funct. Mater., 22, 2027-2039 (2012).*
Bae et al., Sci. Transl. Med., 4(160):1-12 (2012).*
Bellan et al., Adv. Mater., 24:5187-5191 (2012).*
Chong et al., Euro. J. Vasc. Endovasc. Surg., 47(5):566-576 (2014).*
Hoch et al., Euro. J. Cardio-Thor. Surg., 46:767-778 (2014).*
Huang et al., Prog. Nat. Sci: Mater. Internat., 22(2):108-114 (2012).*
Lee et al., Biotechnol. Bioeng., 105: 1178-1186 (2010).*
Xiao et al., Acta Biomater., 7(6):2384-2393 (2011).*
Yang et al., Int. J. Mol. Sci., 12:1936-1963 (2011).*
Zhao et al., Acta Biomater., 26:159-168 (2015).*
Chu et al, "Enhanced growth of animal and human endothelial cells on biodegradable polymers," Biochimica et Biophysica Acta, 1999, p. 479-485, vol. 1472.
Daniel et al, "Endothelial Signal Integration in Vascular Assembly," Annu. Rev. Physiol., 2000, p. 649-671, vol. 62.
O'Donnel et al, "Correlation of operative findings with angiographic and noninvasive hemodynamic factors associated with failure of polytetrafluoroethylene grafts," Journal of Vascular Surgery, 1984, p. 136-148, vol. 1.
Weinberg et al, "A Blood Vessel Model Constructed from Collagen and Cultured Vascular Cells," Science, 1986, p. 397-400, vol. 24.

* cited by examiner

*Primary Examiner* — Thomas J Visone
(74) *Attorney, Agent, or Firm* — Muncy, Geissler, Olds & Lowe, P.C.

(57) ABSTRACT

The present invention provides a reparation method of a tubular vascular graft, (a) immersing a tubular scaffold in a first light sensitivity gelatin solution, and irradiate the tubular scaffold by a first time period, to let surface of the tubular scaffold form a base layer; (b) immersing the tubular scaffold of the step (a) in a chitin gelatin solution, when the surface of the base layer form a film, then immersing the tubular scaffold into a sodium hydroxide solution to generate a middle layer of the surface of the base layer; (c) immersing the tubular scaffold of the step (b) in a second light sensitivity gelatin solution, wherein the second light sensitivity gelatin solution comprises a cell, the tubular scaffold is irradiated by a second time period to form a surface layer of the middle layer; (d) until the cell forms a tubular structure of the surface layer by the cell in the tubular scaffold of the step (c), heating the tubular scaffold by a temperature to solve the base layer into a solution, pulling out the tubular scaffold to get an artificial blood vessels.

8 Claims, 2 Drawing Sheets

TUBULAR VASCULAR GRAFT AND THE PREPARATION THEREOF

FIELD OF THE INVENTION

The present invention provides a preparing method of a tubular vascular graft, which featured as using natural macromolecule material, and the process is simple and quick, low-cost, and the blood vascular lumen size is adjustable.

BACKGROUND OF THE INVENTION

When the blood vessels damaged in clinical, such as thrombosis, vascular stenosis etc., the autologous saphenous vein graft, vascular graft substitute made by synthetic materials are usually used as vascular graft substitutes mostly during the surgery. However, there are some disadvantages of the above vascular graft substitute, such as the limitation of lumen size, and the stability is low and the thrombosis is easily caused, restenosis and severe inflammatory immune is easily occurred again.

The vascular graft substitute used in clinical can be divided into four categories:

(1) Autologous grafts: this is the best choice for clinical vascular graft substitutes, which is obtained from the section of saphenous vein or artery from the patient's chest as a vascular graft substitutes. There is disadvantage that the patients needed this kind of surgery, who usually have preexisting diabetes, hypertension and other related diseases. Therefore, the blood vessels are not healthy and with many existing problems, such as varicose veins, arteriovenous peeling and other conditions. Furthermore, the vein may be achieved from the previous vascular surgery vascular which is not appropriate for use. In addition, if the arterial vessel is replaced by vein, short restenosis rate is very high after transplantation of the vascular graft substitutes due to the different structure and function of blood vessels, therefore, the blood vessel obtained from patients is not quite suitable. Furthermore, the obtained blood vessel lumen size are larger than most coronary caliber (the lumen of coronary arterial is typically less than 4 mm), that would increase the surgical procedure more difficulty during implementing joining. (Reference from: Thomas O. D. et al., 2003)

(2) Allografts, xenografts: other people's blood vessels, umbilical cord, or animal bodies' blood vessels (cattle, pigs, dogs, etc. . . . ) are as vascular graft substitutes after the removal process of cells and cross-linking process. The disadvantage of this type vascular graft substitutes is that the severe inflammation and infection autoimmune response would occur in a short term after transplantation, and the aneurysm would be deteriorate and metastatic phenomenon would occur. (Reference from: Thomas O. D. et al., 2003)

(3) Synthesis of polymer materials: non-biodegradable (nylon, Teflon, Orlon, Dacron, polyethylene (PE), silicon, poly (tetrafluoroethylene) (e-PTFE) and polyurethane (PU) . . . etc.) (Greisler H. P., 1991) and biodegradable (poly-L-lactic acid (PLLA), poly (lactic-co-glycolic acid) (PLGA)) are mainly used as the synthetic material of vascular graft substitutes (Chu F L et al., 1999). The disadvantage of this type vascular graft substitutes is that a non-degradable synthetic material is widely used in large diameter (usually greater than 4 mm diameter vessels), the blood vessel region of high velocity vascular graft substitute. When the vascular graft substitute is used in small-diameter (less than 4 mm) blood vessel region, the vascular restenosis and thrombosis would easily occur due to the material accumulation and excessive intimal proliferation in engaged position. (O'Donnell T F et al., 1984). When the decomposable polymer synthetic materials are used, the product of degradation after transplantation would cause the local peracids of surrounding tissue, and sometimes the chronic inflammation would be caused.

(4) Artificial blood vessels of natural polymer material: vascular graft substitutes are made from the materials contains collagen, animal gelatin, fibrin glue, chitin, hyaluronic acid . . . etc The disadvantage of the vascular graft substitutes made from natural polymeric materials is that there is problem of insufficient mechanical strength and the degradation time is too fast to maintain the structure until autologous cells recover completely. (Reference from: Weinberg C B et al, 1986. Grassi E D et al, 2003.).

In clinical, the need of vascular graft substitutes with high stability, low cost, no limitation of the vessel lumen and high biocompatibility, to be a vascular graft substitutes for damaged blood vessels is urgent.

SUMMARY OF THE PRESENT INVENTION

The present invention provides a preparing method of a tubular vascular graft to solve the problem of lack of mechanical strength of the known artificial blood vessels made by natural macromolecule material, which comprises the following steps:

(a) immersing a tubular scaffold in a first light sensitivity gelatin solution, and irradiate the tubular scaffold by a first time period, to form a base layer on the surface of the tubular scaffold;

(b) immersing the tubular scaffold of the step (a) in a chitin gelatin solution, when the surface of the base layer form a film, then immersing the tubular scaffold into a sodium hydroxide solution to generate a middle layer on the surface of the base layer;

(c) immersing the tubular scaffold of the step (b) in a second light sensitivity gelatin solution, wherein the second light sensitivity gelatin solution comprises a plurality of cells, the tubular scaffold is irradiated by a second time period to form a surface layer on the surface of the middle layer;

(d) until the cells grow as a tubular structure within the surface layer of the step (c), heating the tubular scaffold by a temperature to dissolve the base layer into a solution, removing the tubular scaffold to get an artificial blood vessels. Preferably, the tubular scaffold is heated by 37° C.

Preferably, the first light sensitivity gelatin solution and the second light sensitivity gelatin solution are dissolved in a phosphate solution with a 10% gelatin and a 1% photoinitiator.

Preferably, the gelatin is prepared by a 10 g gelatin solution and a 100 mL phosphate solution, and the 2-methyl-2-propenoic acid anhydride.

Preferably, the gelatin is extracted from the collagen in the animal connective tissue.

Preferably, when the light is ultraviolet, the first time period is 10 seconds.

Preferably, when the chitin gelatin solution is 1% (W/V), the chitin is dissolved in a 1% acetic acid solution.

Preferably, when the light is ultraviolet, the second time period is 12 seconds.

Preferably, the tubular scaffold is, but not limited to, a transparent heat conducting material with a low biological toxicity; preferably, the tubular scaffold is a glass tube.

In one of the embodiment, the cell is, but not limited to, selected from the cell of blood vascular tissue; preferably, the cell is endothelial cell.

The present invention further provides a tubular vascular graft made by the preparation method of the present invention, which comprise a surface layer, which is a second light sensitivity gelatin solution with a tubular structure grew from a plurality of cells; when the tubular vascular graft is transplanted into the biological body, the residual light sensitive gelatin solution would decompose and leave the tubular vascular graft.

In summary, the present invention provides a tubular vascular graft and the preparation method thereof. In comparison to the known art, the present invention provides three advantages:

(1) The preparation method is simple and the time is short, the preparation process time and cost is decreased considerably.

(2) The method of the present invention controls the size of the tubular vascular graft by modifying the lumen of the tubular scaffold, so as to provide an appropriate medical level blood vascular substitute.

(3) The present invention is suitable for the generation of tissue cells, and the light sensitive gelatin solution could be degraded in the biological body, so as to decrease the inflammatory reaction.

In summary, the present invention provides a tubular vascular graft and the preparation method thereof, which is different from the known art, to provide a highly stable, low cost, no limitation of the lumen and high biocompatibility tubular vascular graft, to use as a blood vascular substitute of the damage blood vascular. Besides, the method of the present invention provides a simple, quick, low-cost process and is suitable for all kind of cells.

BRIEF DESCRIPTION OF THE DRAWINGS

The FIG. 1 is the best embodiment of preparation method of tubular vascular graft of the present invention.

The FIG. 2 is the three-dimensional and section view of the tubular structure of the step (c) of the present invention.

SUMMARY OF LABELS IN THE DRAWINGS

| 10 | glass tube |
| 20 | base layer |
| 30 | middle layer |
| 40 | surface layer |
| 410 | endothelial cells |

DETAILED DESCRIPTION

To let skilled in the art fully understand the efficiency of the present invention, the figures and symbols provided herein with the best embodiments to illustrate clearly.

Figure 1:
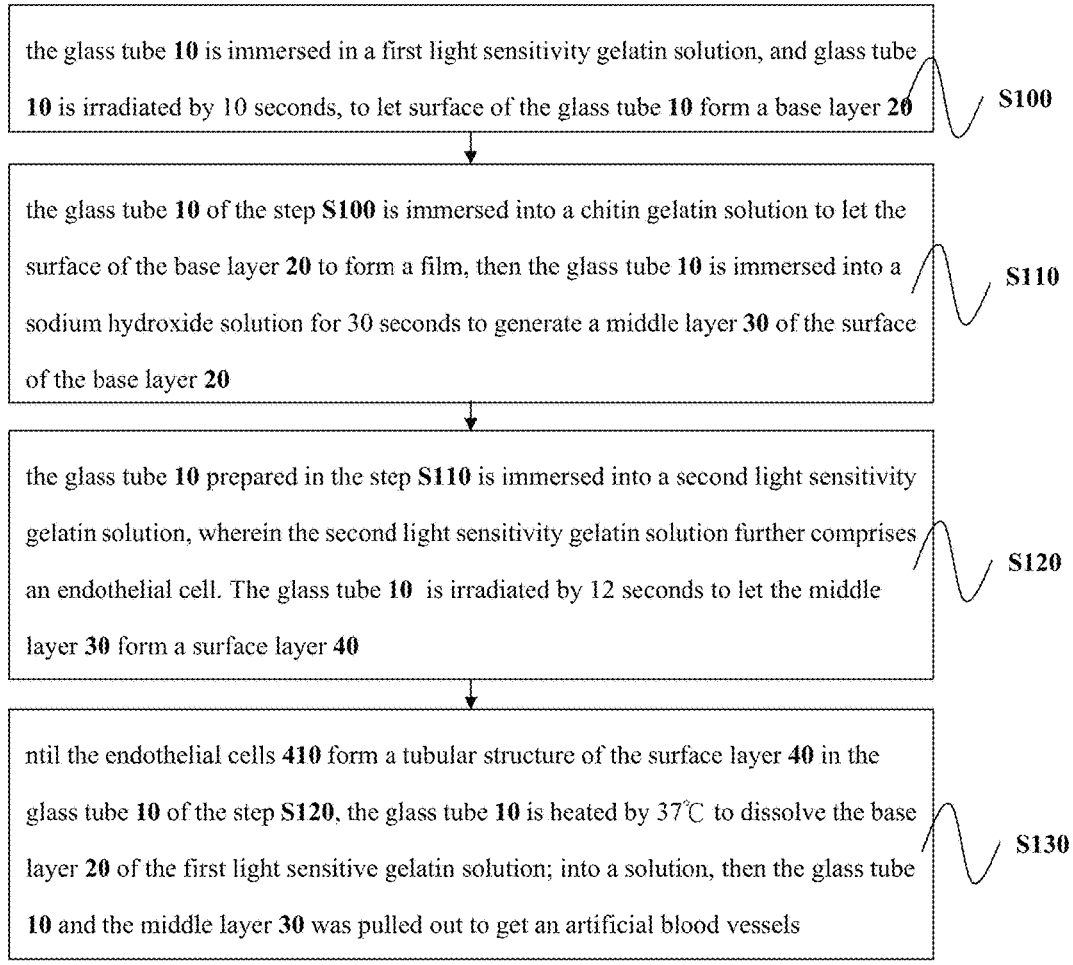

Please refer to the FIG. 1, in the embodiment, the endothelial cell 410 is selected to perform the preparation the tubular vascular graft, which comprises the following steps:

In the step S100, the glass tube 10 is immersed in a first light sensitivity gelatin solution, and glass tube 10 is irradiated by 10 seconds, to form a base layer 20 on the surface of the glass tube 10;

In the step S110, the glass tube 10 of the step S100 is immersed into a chitin gelatin solution to let the surface of the base layer 20 to form a film, then the glass tube 10 is immersed into a sodium hydroxide solution. The chitin gelatin solution (acidic) would neutralize with the sodium hydroxide solution (basic) to enhance the strength of chitin membrane by twisting the molecules chain with opposite electric charge; in one of the embodiment, the 2M sodium hydroxide solution would immersed for 30 seconds to generate a middle layer 30 on the surface of the base layer 20;

In the step S210, the glass tube 10 prepared in the step S110 is immersed into a second light sensitivity gelatin solution, wherein the second light sensitivity gelatin solution further comprises a plurality of endothelial cells. The glass tube 10 is irradiated by 12 seconds to form a surface layer 40 on the middle layer 30;

In the step S130, until the endothelial cells 410 grow as a tubular structure within the surface layer 40 of the step S120, the glass tube 10 is heated by 37° C. to dissolve the base layer 20 of the first light sensitive gelatin solution into a solution, then the glass tube 10 and the middle layer 30 was removed to get an artificial blood vessels.

Figure 2:
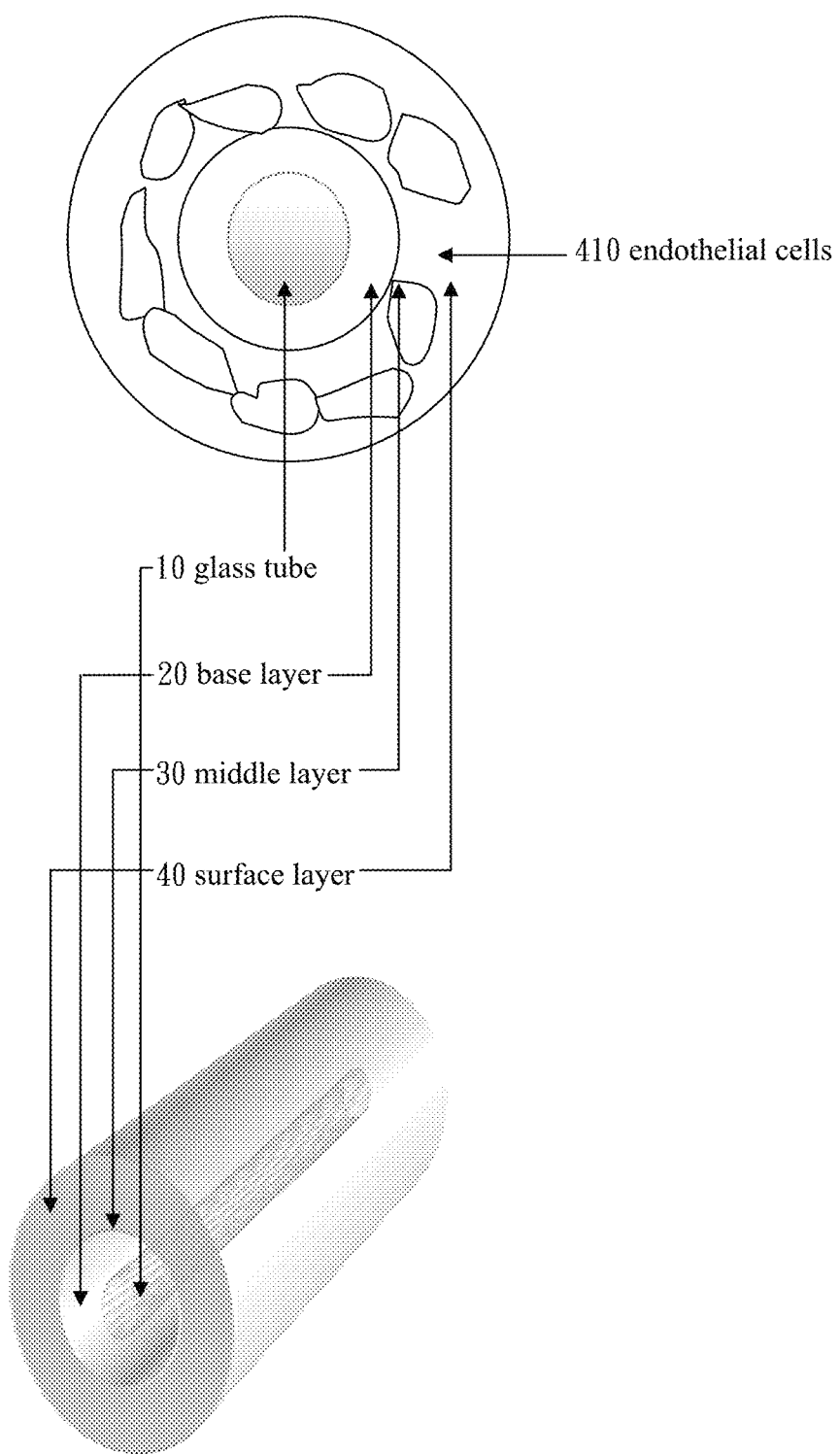

Please refer to FIG. 2, which is the three-dimensional and section view of the tubular structure of the step (c) of the present invention. From inside to outside, the features of the tubular structure is glass tube 10; a base layer 20 which is formed by the first light sensitive gelatin solution; the middle layer 30 which is prepared by the chitin gelatin solution; and the surface layer 40 which is comprised by the second light sensitive gelatin solution and is comprising a plurality of endothelial cells 410.

As mentioned in the previous embodiment, the tubular vascular graft of the present invention featured as the surface layer 40, which comprises a plurality of tubular structured endothelial cells; when the tubular vascular graft is transplanted into the biological body in the surgery, the light sensitive gelatin solution would be decomposed in the biological body and leave the endothelial cells to impair the original damaged blood vascular.

Preferably, the e first light sensitive gelatin solution and the second light sensitive gelatin solution can be prepared by, but not limited to, collagen, animal gelatin, fibrin, chitin or hyaluronic acid.

As mentioned in the previous embodiment, the first light sensitive gelatin solution and the second light sensitive gelatin solution are dissolved in a phosphate solution with a 10% gelatin and a 1% photoinitiator; wherein the gelatin is prepared by a 10 g gelatin solution and a 100 mL phosphate solution, and the 2-methyl-2-propenoic acid anhydride; the gelatin solution is extracted from the collagen in the animal connective tissue, such as pig skin or cowhide.

As mentioned in the previous embodiment, the chitin is dissolved in a 1% acetic acid solution; and the molecular weight of the chitin is 190,000-310,000.

As mentioned above, the embodiment is irradiated by ultraviolet light with different time period to control the crosslink reaction of the light sensitive gelatin solution, the irradiation time period of the light sensitive gelatin solution in the base layer 20 is shorter, which could make the base layer stick on the glass tube 10. In the present invention, the temperature is also controlled to make part of the light sensitive gelatin dissolve into liquid at specific temperature, at this time, the glass tube 10 and the middle layer 30 could be pulled out to make the hallow blood vascular product. Besides, when the endothelial cells 410 form a compact structure tissue, the light sensitive gelatin solution would be decomposed gradually in the biological body and leave the endothelial cells to impair the original damaged blood vascular.

What is claimed is:

1. A method of preparing a tubular vascular graft, which comprises the steps:

immersing a tubular scaffold in a first light sensitive gelatin solution, and irradiating the tubular scaffold by a first time period, to form a base layer on the surface of the tubular scaffold;

immersing the tubular scaffold of the step (a) in a chitin gelatin solution, when the surface of the base layer form a film, then immersing the tubular scaffold into a sodium hydroxide solution to generate a middle layer on the surface of the base layer;

immersing the tubular scaffold of the step (b) in a second light sensitivity gelatin solution, wherein the second light sensitivity gelatin solution comprises a plurality of cells, the tubular scaffold is irradiated by a second time period to form a surface layer on the surface of the middle layer;

until the cells grow as a tubular structure within the surface layer of the step (c), heating the tubular scaffold by a temperature to dissolve the base layer into a solution, removing the tubular scaffold to get an artificial blood vessel.

2. The method of claim 1, wherein the first sensitive gelatin solution and the second light sensitivity gelatin solution are dissolved in a phosphate solution comprising 10% gelatin and 1% photoinitiator.

3. The method of in claim 2, wherein the gelatin solution is prepared from a 10 g gelatin solution, a 100 mL phosphate solution, and the 2-methyl-2-propenoic acid anhydride.

4. The method of in claim 3, wherein the gelatin is extracted from collagen in animal connective tissue.

5. The method of in claim 1, wherein if the light is ultraviolet, the first time period is 10 seconds.

6. The method of in claim 1, wherein if the chitin gelatin solution is 1% (W/V), the chitin is dissolved in a 1% acetic acid solution.

7. The method of in claim 1, wherein if the light is ultraviolet, the second time period is 12 seconds.

8. The method of in claim 1, wherein the tubular scaffold is a transparent heat conducting material with a low biological toxicity.

* * * * *